(12) United States Patent
Demuth et al.

(10) Patent No.: US 6,583,327 B2
(45) Date of Patent: Jun. 24, 2003

(54) CONTINUOUS ISOTHERMAL PROCESS FOR PREPARING MONONITROTOLUENES

(75) Inventors: Ralf Demuth, Hilden (DE); Frank Döbert, Köln (DE); Harald Petersen, Dormagen (DE); Georg Ronge, Düsseldorf (DE); Hans-Martin Weber, Leverkusen (DE); Thomas Würminghausen, Leverkusen (DE); Eberhard Zirngiebl, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/032,760

(22) Filed: Oct. 26, 2001

(65) Prior Publication Data

US 2002/0091290 A1 Jul. 11, 2002

(30) Foreign Application Priority Data

Nov. 8, 2000 (DE) .......................... 100 55 359

(51) Int. Cl.[7] ........................................... C07C 205/00
(52) U.S. Cl. ........................................ 568/940; 568/939
(58) Field of Search .................................. 568/939, 940

(56) References Cited

U.S. PATENT DOCUMENTS

| 2,256,999 A | * | 9/1941 | Castner et al. .............. 260/645 |
| 4,772,757 A | | 9/1988 | Lailach et al. .............. 568/939 |
| 5,275,701 A | * | 1/1994 | Mazzafro et al. ............. 203/12 |
| 5,648,565 A | * | 7/1997 | Konig et al. ................ 568/940 |
| 5,763,697 A | | 6/1998 | Hermann et al. ........... 568/939 |

OTHER PUBLICATIONS

Kirk–Othmer, Encyclopedia of Chemical Technology, 4th edition, vol. 17, (month unavailable), 1996, Nitrobenzene and Nitrotoluenes, pp. 133–152.

Kirk–Othmer, Encyclopedia of Chemical Technology, 4th edition, vol. 17, (month unavailable), 1996, Nitration, pp. 68–80.

* cited by examiner

Primary Examiner—J. Parsa
(74) Attorney, Agent, or Firm—Godfried R. Akorli; Diderico van Eyl

(57) ABSTRACT

The present invention relates to a process for the continuous isothermal preparation of mononitrotoluenes with concentration of the resultant waste sulfuric acid and recycling of the concentrated waste sulfuric acid to the process.

11 Claims, No Drawings

CONTINUOUS ISOTHERMAL PROCESS FOR PREPARING MONONITROTOLUENES

BACKGROUND OF THE INVENTION

The present invention relates to a continuous isothermal process for preparing mononitrotoluenes with concentration of the resultant waste sulfuric acid and recycling of the concentrated waste sulfuric acid into the process.

Mononitrotoluenes are important intermediates for preparing optical brighteners, plant protection agents, and pharmaceutical products. Mononitrotoluenes are prepared, for example, on an industrial scale, by isothermal nitration of toluene. In this process toluene is reacted with a mixture of sulfuric acid and nitric acid (mixed acid, nitrating acid) (see, for example, Kirk-Othmer, Encyclopedia of Chemical Technology Vol. 17, 4th edition 1996, "Nitration" and "Nitrobenzenes and Nitrotoluene").

The reaction produces a considerable amount of waste sulfuric acid that is polluted with organic compounds (for example, dinitrotoluenes or nitrated cresols) and as a result the acid must be worked up in a manner that is intensive with respect to process and costs. To avoid the production of waste acid, processes have been developed that comprise concentration of sulfuric acid, the concentrated sulfuric acid being freed from water and organic compounds and then recycled in a circulation process back to the nitration reaction.

DE 195 39 205 A discloses process parameters for the mononitration of aromatics, the mixed acids being adapted to the properties of the aromatic to be nitrated in such a way as to produce an approximately 70% strength waste sulfuric acid. In addition, the use of partially concentrated waste acids having a sulfuric acid concentration between 85% and 92% is described.

U.S. Pat. No. 4,772,757 describes a process for preparing nitrobenzene in which the resultant waste acid is concentrated to 75 to 92% and recycled back to the nitration process. Since toluene, due to the methyl group, compared with benzene, is markedly more oxidation-sensitive and has a tendency in the nitration to form by-products, applying the reaction conditions for the nitration of benzene to the nitration of toluene involves the expectation of an increase in the amount of unwanted by-products.

Due to the solubility of organic compounds in sulfuric acid, organic by-products such as oxalic acid or benzoic acid accumulate in concentrated waste acids that are recycled to the nitration reaction. In addition, accumulation of nitrosylsulfuric acid can occur. The decomposition of these organic by-products and the heat of decomposition released in the course of this reaction lead to unwanted decomposition of the reaction product nitrotoluene. In addition, there is an adverse effect on the space-time yield, since the organic by-products can react with the nitric acid used in oxidative degradation reactions and thus some of the nitric acid is no longer available for the actual nitration.

To avoid accumulation of organic by-products in the concentrated waste sulfuric acid, this can be highly concentrated (which is to say, can be concentrated to about 96%). Under these concentration conditions the organic by-products are destroyed. Nitrosylsulfuric acid can be removed from the concentrated waste sulfuric acid by blasting with sulfur dioxide.

A disadvantage of concentrating waste sulfuric acid to 96% is that concentration must be carried out at temperatures of approximately 250° C., which, in industrial scale reactions, leads to an increased energy consumption. In addition, waste sulfuric acid that is concentrated to 96% must be diluted in an additional reaction step before recycling to the nitration reaction, the dilution generally being carried out by mixing with non-concentrated waste acid. Blowing out nitrosylsulfuric acid must be carried out in an additional process step, disadvantageously.

There was therefore a requirement for a continuous isothermal process for preparing mononitrotoluene that permits inexpensive concentration of the waste sulfuric acid with subsequent recycling into the nitration reaction in the context of a circulation process, without organic by-products accumulating in the concentrated sulfuric acid.

SUMMARY OF THE INVENTION

Surprisingly, a continuous process has been found for preparing mononitrotoluenes by reacting toluene with nitric acid and sulfuric acid under isothermal reaction conditions comprising (a) feeding 75 to 93% strength sulfuric acid, 60 to 70% strength nitric acid, and toluene into a reactor, (b) separating the crude nitrotoluene from the waste sulfuric acid at the reactor outlet, (c) concentrating the waste sulfuric acid in a single-stage concentration to 75 to 93%, and (d) recycling the concentrated waste sulfuric acid in a circulation back to the nitration reaction.

DETAILED DESCRIPTION OF THE INVENTION

The concentrated waste sulfuric acid present in the inventive process, even after repeated circulation, exhibits no accumulation of organic by-products such as oxalic acid or benzoic acid or of inorganic compounds such as nitrosylsulfuric acid. Furthermore, in the inventive process, advantageously, a dilute nitric acid is used, as a result of which the process can be operated particularly inexpensively. Despite relatively high amounts of water that are necessitated by using dilute nitric acid, the reaction proceeds with high reaction rates. Surprisingly, in addition, a reaction-accelerating effect is observed due to the circulation of the waste sulfuric acid concentrated by the inventive process.

In the inventive process, preferably a 75 to 93% strength sulfuric acid, particularly preferably an 84 to 89% strength sulfuric acid, is used. The nitric acid used is preferably a 60 to 70% strength nitric acid, particularly preferably a 65 to 68% strength nitric acid. The proportion of nitric acid in the sulfuric acid/nitric acid mixture is given by presetting the concentration of the sulfuric acid and nitric acid and the concentration of the concentrated sulfuric acid and is preferably approximately 15 to 25%, particularly preferably approximately 17 to 20%.

In the inventive process, preferably 0.98 to 1.1 equivalents of toluene (particularly preferably 1.01 to 1.05 equivalents of toluene), based on one equivalent of nitric acid, are used. Even with a toluene excess, based on nitric acid, in the inventive process, surprisingly, no black coloration of the circulation waste sulfuric acid (black spent acid) occurs, an effect that is otherwise observed under these conditions.

The starting materials nitric acid, sulfuric acid, and toluene used in the inventive process are preferably intensively mixed using the mixing elements known in the art. Mixing elements that can be used are, for example, static mixers, pumps, jets, agitators, or combinations of such mixing elements.

The inventive process is carried out continuously under isothermal conditions in a reactor. Reactors that are used are preferably commercially available reactors, for example, tubular reactors, loop reactors, stirred tanks, or combinations of loop reactors and stirred tanks.

In a further preferred embodiment, the inventive process is carried out in multi-stage reactor cascades.

The inventive process is carried out under isothermal conditions, the reaction temperature preferably being in the range from 20 to 80° C., particularly preferably in the range from 30 to 70° C., and very particularly preferably in the range from 40 to 65° C.

At the reactor outlet, the sulfuric acid concentration in the waste sulfuric acid is preferably 60 to 80%, particularly preferably 65 to 75%, and very particularly preferably 69 to 73%. The waste sulfuric acid is virtually free from nitric acid and, in addition to sulfuric acid, contains water, organic compounds (for example, dinitrotoluenes or nitrated cresols), and, if appropriate, nitrous acid.

The crude nitrotoluene is separated from the waste sulfuric acid preferably using a static settler or a separator.

By concentrating the waste sulfuric acid carried out in the inventive process, this waste sulfuric acid is substantially freed from water and organic compounds, the organic compounds either being removed from the waste sulfuric acid or destroyed so that volatile compounds (for example, $CO_2$), are formed and discharged from the waste sulfuric acid.

The single-stage concentration is preferably carried out in an evaporator. In order to obtain the inventive concentration of 75 to 93% (preferably 84 to 89%), the evaporator is preferably operated at a pressure of 50 to 300 mbar, particularly preferably 60 to 200 mbar, and very particularly preferably 80 to 150 mbar. The temperature of the waste sulfuric acid in the evaporator outlet is preferably 100 to 200° C., particularly preferably 150 to 190° C., and very particularly preferably 160 to 180° C. The temperature of the effluent concentrated waste sulfuric acid is preferably used to heat, in a countercurrent heat exchanger, the waste sulfuric acid flowing into the evaporator. In this variant, the waste sulfuric acid flowing into the evaporator is preferably heated by the countercurrent flow so that it is superheated at the evaporator pressure and thus a portion of the water and small amounts of the acid vaporize (flash evaporation) without additional heat supply.

For the single-stage concentration in the inventive process, preferably a commercially available single-stage cascade evaporator having a tantalum tube bundle is used, such that, with each cascade, the concentration of acid coming from the inlet is increased, so that in the first cascades there is a relatively low concentration of acid. Advantages of the low concentration in the first cascade are, first, that the boiling point is still low and thus there is a high driving temperature difference for the heat transfer (smaller evaporator) and, second, that at low acid concentrations, any nitrosylsulfuric acid present in the waste sulfuric acid can readily be removed from the reaction. Thus, by using a single-stage cascade evaporator in the inventive process, blowing out the nitrosylsulfuric acid using sulfur dioxide is avoided, thus avoiding an additional process step.

Preferably a stripping part is used in order to achieve particularly good reduction in the content of organic compounds and/or the content of nitrosylsulfuric acid. A distillation column section provided with distillation internals is termed the stripping part, to which is passed, from the top, the waste sulfuric acid, which is liquid or somewhat superheated at evaporator pressure, and is operated in countercurrent from the bottom with the vapor ascending from the evaporator. Distillation internals that can be used in the stripping part are column internals known to those skilled in the art, for example, trays, arranged packings, and dumped packings. In a preferred embodiment, low pressure-drop distillation internals such as arranged packings or dumped packings are used. The residence time in the stripping part, in the case of simultaneously low acid concentration, together with the mass transfer that is made more intensive by the distillation internals, advantageously leads to a rapid destruction and removal of organic and inorganic compounds.

The crude nitrotoluene obtained in the inventive process generally comprises less than 0.5% dinitrated compounds and less than 0.8% dinitrocresols.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

In a miniplant installation, 0.80 kg of 87.7% strength sulfuric acid, 0.31 kg of 67% strength nitric acid, and 0.32 kg of toluene were fed per hour to a stirred-tank cascade. The temperature in the stirred tanks was approximately 40° C. After the reaction was terminated, the crude nitrotoluene was separated from the waste sulfuric acid by means of a static settler. The waste sulfuric acid was fed via a preheater to an evaporator and concentrated to 87.7% at 100 mbar and 168° C., with organic compounds being distilled off or destroyed. The waste sulfuric acid was fed back to the nitration reaction.

The resultant crude nitrotoluene had the following composition: 3.27% toluene, 57.58% ortho-nitrotoluene, 4.13% meta-nitrotoluene, 34.68% para-nitrotoluene, 0.08% dinitrotoluene, and 0.38% dinitrocresol.

Example 2

3,000 liters of approximately 97% strength toluene that contained small amounts of nitrated toluenes and cresols, 3,700 liters of 87% strength sulfuric acid, and 1,800 liters of 67 to 68% strength nitric acid were fed per hour to a cascade of a plurality of loop reactors. The reactors were operated between 43 and 47° C. After the reaction was terminated, the crude nitrotoluene was separated from the waste sulfuric acid by means of a separator. The waste sulfuric acid was concentrated back to the initial value of 87% at approximately 170° C. and 100 mbar and recycled to the nitration reaction.

The resultant crude nitrotoluene had the following composition: 4.13% toluene, 57.12% ortho-nitrotoluene, 4.18% meta-nitrotoluene, 34.17% para-nitrotoluene, 0.12% dinitrotoluene, and 0.71% cresols.

Comparative Example 1

188 kg of 70% strength sulfuric acid, 8.1 kg of 67% strength nitric acid, and 8.6 kg of toluene were fed continuously per hour to a tubular reactor. The reaction was carried out under adiabatic conditions. After separating off the crude nitrotoluene, the waste sulfuric acid was concentrated to the starting concentration of 70% in an evaporator at 60 mbar and 90° C. The concentrated waste sulfuric acid was fed back to the nitration reaction.

Compared with the inventive examples, after a few hours marked accumulation of organic compounds (oxalic acid as main component) was observed in the circulated acid.

Comparative Example 2

2,940 liters of approximately 72 to 73% strength used sulfuric acid, 1,830 liters of 98% strength nitric acid, and 4,700 liters of toluene that contained approximately 3% of nitrated toluenes and cresols were fed per hour to a continuous reactor cascade. The reaction was carried out at 44 to 54° C. After separating off the crude nitrotoluene, a portion of the waste sulfuric acid was fed back to the nitration reaction, and the remainder was subjected to two-stage concentration to 96% sulfuric acid and also fed back to the nitration reaction.

The resultant crude nitrotoluene had the following composition: 4.48% toluene, 56.38% ortho-nitrotoluene, 4.28% meta-nitrotoluene, 34.20% para-nitrotoluene, 0.58% dinitrotoluene, and 0.73% cresols. Compared with the inventive examples, significantly higher amounts of unwanted dinitrotoluene were present in the crude nitrotoluene obtained.

What is claimed is:

1. A continuous process for preparing mononitrotoluenes by reacting toluene with nitric acid and sulfuric acid under isothermal reaction conditions comprising
   (a) feeding 75 to 93% strength sulfuric acid, 60 to 70% strength nitric acid, and toluene into a reactor,
   (b) separating the crude nitrotoluene from the waste sulfuric acid at the reactor outlet,
   (c) concentrating the waste sulfuric acid in a single-stage concentration to 75 to 93%, and
   (d) recycling the concentrated waste sulfuric acid in a circulation back to the nitration reaction.

2. A process according to claim 1 wherein 84 to 89% strength sulfuric acid is used.

3. A process according to claim 1 wherein 65 to 68% strength nitric acid is used.

4. A process according to claim 1 wherein 0.98 to 1.1 equivalents of toluene, based on one equivalent of nitric acid, are used.

5. A process according to claim 1 wherein 1.01 to 1.05 equivalents of toluene, based on one equivalent of nitric acid, are used.

6. A process according to claim 1 wherein the sulfuric acid concentration at the reactor outlet is 60 to 80%.

7. A process according to claim 1 wherein the concentration of waste sulfuric acid is carried out in an evaporator at a pressure of 60 to 200 mbar and a temperature of 100 to 200° C.

8. A process according to claim 1 wherein the concentration of waste sulfuric acid is carried out in a cascade evaporator.

9. A process according to claim 7 wherein the evaporator is operated with a stripping part.

10. A process according to claim 8 wherein the evaporator is operated with a stripping part.

11. A process according to claim 1 wherein the reaction temperature is in the range from 20 to 80° C.

* * * * *